United States Patent
Kaiser et al.

(10) Patent No.: US 11,938,344 B2
(45) Date of Patent: Mar. 26, 2024

(54) BEAM PATH BASED PATIENT POSITIONING AND MONITORING

(71) Applicant: Brainlab AG, Munich (DE)

(72) Inventors: Hagen Kaiser, Munich (DE); Michael Stead, Munich (DE)

(73) Assignee: Brainlab AG, Munich (DE)

( * ) Notice: Subject to any disclaimer, the term of this patent is extended or adjusted under 35 U.S.C. 154(b) by 556 days.

(21) Appl. No.: 17/255,558

(22) PCT Filed: Jul. 8, 2019

(86) PCT No.: PCT/EP2019/068274
§ 371 (c)(1),
(2) Date: Dec. 23, 2020

(87) PCT Pub. No.: WO2020/020623
PCT Pub. Date: Jan. 30, 2020

(65) Prior Publication Data
US 2021/0339050 A1    Nov. 4, 2021

(30) Foreign Application Priority Data

Jul. 24, 2018 (WO) .................. PCT/EP2018/070062

(51) Int. Cl.
*A61N 5/10* (2006.01)
(52) U.S. Cl.
CPC .......... *A61N 5/1049* (2013.01); *A61N 5/107* (2013.01); *A61N 2005/105* (2013.01)
(58) Field of Classification Search
CPC ........ A61N 5/10; A61N 5/1049; A61N 5/107; A61N 2005/105
See application file for complete search history.

(56) References Cited

U.S. PATENT DOCUMENTS

2006/0020195 A1    1/2006    Falco et al.
2009/0251709 A1 *  10/2009   Kindlein ............... A61N 5/1049
                                              356/602
(Continued)

FOREIGN PATENT DOCUMENTS

EP    2098169 A2    9/2009

OTHER PUBLICATIONS

Tsoli et al., "Breathing Life into Shape: Capturing, Modeling and Animating 3D Human Breathing", Max Planck Institute for Intelligent Systems, Tubingen, Germany. Jul. 2014. 11 pages.

(Continued)

*Primary Examiner* — Jurie Yun
(74) *Attorney, Agent, or Firm* — Tucker Ellis LLP

(57) ABSTRACT

Provided is a method of positioning a patient for radiation treatment and/or of monitoring a position of the patient during radiation treatment. The method includes providing surface data from a 3D surface scanner indicative of a surface of a body part of the patient to be irradiated in the radiation treatment. Surface data are calibrated with respect to a relative position of the 3D surface scanner and an isocenter position of a radiation treatment apparatus. A beam path of a radiation beam is determined based on planning data for the radiation treatment and intersected with a part of the surface of the patient represented by the surface data. Further, at least a first portion of the patient's surface located inside the beam path and/or at least a second portion of the patient's surface located outside the beam path is calculated.

15 Claims, 4 Drawing Sheets

(56) References Cited

U.S. PATENT DOCUMENTS

2010/0008467 A1    1/2010  Dussault et al.
2011/0154569 A1*   6/2011  Wiggers ............... G05D 1/0276
                                              5/81.1 R

OTHER PUBLICATIONS

International Preliminary Report on Patentability for corresponding International Application No. PCT/EP2019/068274, dated Feb. 4, 2021. 7 Pages.
International Search Report and Written Opinion for corresponding International Application No. PCT/EP2019/068274, dated Oct. 11, 2019. 8 Pages.

* cited by examiner

BEAM PATH BASED PATIENT POSITIONING AND MONITORING

RELATED APPLICATION DATA

This application is a national phase application of International Application No. PCT/EP2019/068274 filed Jul. 8, 2019, which claims priority to International Application No. PCT/EP2018/070062, filed on Jul. 24, 2018, the contents of both of which are incorporated herein by reference.

FIELD OF THE INVENTION

Generally, the present invention relates to the field of radiation treatment. More specifically, the present invention relates to a computer-implemented medical method of positioning a patient for radiation treatment and/or of monitoring a position of a patient during radiation treatment. The invention further relates to a corresponding computer program, a non-transitory program storage medium storing such a program and a computer for executing the program, as well as a medical system comprising an electronic data storage device and/or the aforementioned computer.

TECHNICAL BACKGROUND

For radiation treatment, irradiation treatment or radiotherapy using a radiation beam or beam of ionizing radiation, correct positioning of the patient and/or a body part of the patient that is to be irradiated in the radiation treatment can be a challenging task. This can be particularly true if the body part to be irradiated comprises soft tissue or non-rigid tissue, such as e.g. the breast, because the body part or at least a part thereof may be subject to deformations or displacements. For instance, in breast cancer therapy the radiotherapy usually comprises a sequence of radiation treatments or radiation sessions in order to deliver a prescribed dose to the cancerous tissue. This dose is usually determined beforehand for all radiation sessions or treatments based on a predefined position of the patient with respect to an isocenter or isocenter position of a radiation treatment apparatus. The predefined position of the patient is also referred to as target position or reference position.

In order to position the patient for the actual radiation treatment, surface scanners can be utilized, which allow to detect and/or visualize a current position or current surface of the patient (or a part thereof). Apart from that, usually a reference image or reference surface of at least a part of the patient located at the target position is displayed on a user interface in order to visualize the target position. The reference image can, for instance, be a recorded surface of at least a part of the patient or at least a part of a recorded computed tomography, CT, scan of the patient located at the target position. The current position or surface, as detected by the surface scanner, can then be displayed in the same coordinate system on the user interface as the reference image. A couch or any other patient support structure or unit of the radiation treatment apparatus can then be moved accordingly until the current patient surface matches at least a part of the reference image, thereby preferably positioning the patient at the target position.

By means of this approach, rigid body parts of the patient usually can be accurately positioned with respect to the target position, as the rigid parts may not be subject to deformations with respect to the reference image. On the other hand, non-rigid body parts, such as e.g. the breast, may be deformed or displaced with respect to the reference image. Such deformation may, for example, result from swelling of the non-rigid body part due to a previous treatment session or due to a movement or displacement of the non-rigid body part with respect to its location in the reference image. Accordingly, aligning non-rigid body parts with the reference image can be challenging.

To address this aspect, the non-rigid parts of the patient can, for instance, be masked in the current surface as detected by the surface scanner, such that these parts can be disregarded when positioning the patient. In this case, however, the body part that is to be irradiated, such as the breast, is disregarded, which might affect effectiveness of the treatment. Alternatively, deviations of the current surface of the non-rigid body parts with respect to the reference image or reference surface can be visualized on the user interface, thereby encouraging a user (e.g. medical staff) to correct for the deviations by a corresponding movement or displacement of the patient. Depending on the extent of the deformation or displacement of the non-rigid body part with respect to the reference image, such movement can result in uncomfortableness for the patient or it can even be impossible to correctly align the non-rigid body parts with the reference image, e.g. if the breast is highly swollen.

Apart from the correct positioning of a patient for the radiation treatment, which is also referred to as patient setup, the patient and/or the body part to be irradiated should preferably remain at the target position during the actual radiation treatment. Particularly when irradiating non-rigid body parts, such as the breast, also this can be a challenging task due to movements and/or displacements of the body parts that can result from e.g. a breathing or any other movement of the patient.

It is, therefore, desirable to provide for an improved method of positioning a patient for radiation treatment and/or an improved method of monitoring the position of the patient during the radiation treatment, e.g. allowing to eliminate or at least alleviate the aforementioned drawbacks.

The present invention can be used for radiation treatment or radiotherapy procedures e.g. in connection with a system for image-guided radiotherapy such as VERO® and ExacTrac®, both products of Brainlab AG.

Aspects of the present invention, embodiments, examples, exemplary features and exemplary steps are disclosed in the following. Different aspects, embodiments, examples, exemplary features and exemplary steps of the invention can be combined in accordance with the invention wherever technically expedient and feasible.

EXEMPLARY SHORT DESCRIPTION OF THE INVENTION

In the following, a short description of the specific features of the present invention is given which shall not be understood to limit the invention only to the features or a combination of the features described in this section.

The disclosed method comprises providing surface data acquired by means of a three-dimensional, 3D, surface scanner of a surface of at least a body part of the patient, which body part is to be irradiated in a radiation treatment, in a radiation treatment session and/or by way of radiotherapy. The surface data are calibrated with respect to a relative position of the 3D surface scanner and an isocenter or isocenter position of a radiation treatment apparatus. A beam path and/or frustum of a radiation beam is determined based on planning data for the radiation treatment and intersected with at least a part of the surface of the patient represented by the surface data. Further, at least a portion of the patient's surface located inside and/or outside the beam path is calculated.

Generally, this allows to correctly position the patient and/or the body part to be irradiated with respect to the isocenter position and/or with respect to the beam path. Accordingly, patient setup in preparation of the actual treatment as well as monitoring of the patient's position during the treatment can be significantly improved.

Moreover, based on segmentation of at least a part of the surface data an amount of surface of the body part to be irradiated located inside and/or outside the beam path can be determined, calculated and/or visualized. Such information can, for instance, be used for providing guidance to the user (e.g. medical staff) on how to position the patient for the radiation treatment. Apart from that, such information can be used for controlling the radiation treatment apparatus, e.g. the patient support unit and/or a beam source, such that the effectiveness of the overall treatment may be improved. Also, a dose deposition in healthy tissue, which may e.g. arise from an incorrect positioning of the patient, may be reduced or avoided.

The present invention may be of particular advantage if the body part to be irradiated comprises non-rigid tissue, soft tissue, and/or tissue located near or adjacent the surface or skin of the patient, such as for example the breast or the heel bone. Such body parts can be subject to deformations and/or displacements. Hence, it may be more difficult to correctly position non-rigid body parts than rigid body parts, such as body parts comprising bone material. It is emphasized, however, that the invention is not restricted to radiation treatment of non-rigid body parts, such as breast or heel bone cancer therapy, but rather can be applied to any other type of radiotherapy.

GENERAL DESCRIPTION OF THE INVENTION

In the following section, a description of the general features of the present invention is given, for example by referring to possible embodiments of the invention.

As set out hereinabove, it may be desirable to provide for an improved method of positioning a patient for radiation treatment and/or of monitoring the position of the patient during the radiation treatment, e.g. allowing to more precisely monitor and/or control the patient's position.

This is achieved by the subject-matter of the independent claims, wherein further embodiments are incorporated in the dependent claims and the following description.

According to a first aspect of the invention, there is provided a computer-implemented medical method of positioning a patient for a radiation treatment and/or a computer-implemented medical method of monitoring a position of a patient during a radiation treatment. The method according to the first aspect may alternatively or additionally refer to a computer-implemented medical method of monitoring a radiation treatment of the patient. The method comprises the following steps:

providing surface data from a three-dimensional, 3D, surface scanner, wherein the surface data are indicative and/or representative of a surface of at least a part of a body part of the patient to be irradiated in the radiation treatment, and wherein the surface data are calibrated with respect to a relative position of the 3D surface scanner and an isocenter and/or an isocenter position of a radiation treatment apparatus;

reconstructing, particularly computationally reconstructing, and/or determining a beam path of a radiation beam based on planning data for the radiation treatment and/or based on processing the planning data; and calculating and/or computing, based on intersecting at least a part of the surface of the body part and the reconstructed beam path, at least a first portion of the surface of the body part located inside the beam path and/or at least a second portion of the surface of the body part located outside the beam path.

By intersecting the surface of at least a part of the body part, as represented by the surface data, with the reconstructed beam path, a position of the body part to be irradiated with respect to the actual radiation beam can be estimated or determined. This, in turn, allows to precisely and correctly position the patient for the radiation treatment, e.g. such that a volume of the body part to be irradiated in the radiation treatment can be optimized and/or maximized.

The beam path or the reconstructed beam path may, generally, refer to a volume covered by the radiation beam, as estimated, calculated and/or computed based on the planning data and/or as derived therefrom. In other words, the reconstructed beam path may refer to a volume, e.g. expectedly, covered by the radiation beam during the radiation treatment. The beam path or reconstructed beam path may also be referred to as frustum (or set of frustums) hereinafter. The reconstructed beam path may have an arbitrary geometry, such as e.g. conical, pencil-beam like, polygonal, rectangular, cylindrical or the like. Particularly, the beam path may be reconstructed three-dimensionally. Accordingly, the reconstructed beam path may be given in spatial coordinates and/or may be mapped to spatial coordinates, e.g. spatial coordinates relative to the isocenter position. Therein, the isocentre or isocenter position may denote a location or position where different radiation beams of the radiation treatment apparatus, such as e.g. different beams at different beam angles, intersect each other.

The 3D surface scanner may refer to any device or arrangement of devices configured to determine and/or detect the surface of the patient and/or at least a part of the body part. The 3D surface scanner may comprise one or more sensors, such as e.g. one or more cameras, a stereo camera, a 3D camera, a time of light sensor, a LIDAR sensor, a depth camera, a distance sensor, a laser sensor and/or any other type of sensor. The 3D surface scanner may also comprise a thermo-camera and/or infrared camera. Data and/or signals from a plurality of sensors may be fused to provide the surface data.

Generally, the surface data may refer to an arbitrary abstraction or representation of the surface of the body part of the patient. For instance, the surface data may refer to and/or comprise points in three-dimensional space. Accordingly, the surface data may refer to one or more point clouds in 3D space. Alternatively or additionally, the surface data may comprise any other suitable representation of the surface, such as e.g. one or more mathematical formulas describing the surface and/or a mesh structure describing the surface.

The term "calibrated surface data" and/or "calibrated with respect to a relative position of the 3D surface scanner and the isocenter" may mean that the surface data are provided relative to the isocenter or isocenter position and/or that the surface data contain an information about the isocenter position. For example, the 3D surface scanner may be calibrated to the isocenter position, such that raw surface data output by the 3D surface scanner may be provided as surface data relative to the isocenter position. Alternatively, raw surface data of the 3D surface scanner may be processed and/or transformed, e.g. based on coordinate transformation, to the surface data relative to the isocenter position.

Therein, the surface data of the 3D surface scanner may be provided online by the 3D surface scanner. In other words, the surface data may be retrieved directly from the 3D surface scanner, e.g. while the 3D surface scanner is capturing the surface of the body part and/or at least a part of the patient. Alternatively or additionally the surface data may be buffered and/or stored on a data storage device.

Re-phrasing the first aspect of the invention, surface data of at least a part of the patient, particularly at least a part of the body part to be irradiated, are provided by means of a 3D surface scanner. Therein, the body part may be any part of the patient, such as e.g. a part of a breast, an entire breast, a part of a heel, an entire heel or any other part of the patient to be treated in the radiation treatment. The surface data of the at least part of the body part to be irradiated and/or the surface represented by the surface data is intersected with the reconstructed beam path. For this purpose, the surface data and/or the surface represented by the surface data may be given relative to the isocenter position and/or in an isocenter coordinate system, i.e. a coordinate system in which the isocenter position is known. Also the beam path may be given in this coordinate system and/or may be reconstructed relative to the isocenter position, wherein the beam path may represent the volume covered by the actual radiation beam during the treatment, as derived from and/or estimated based on the planning data.

Based on intersecting the surface represented by the surface data with the reconstructed beam path, the at least first portion of the surface located inside the beam path can be calculated. Therein, the term "located inside" may mean that the first portion of the surface is arranged within the volume covered by the radiation beam that is represented by the reconstructed beam path and/or that the first portion is located at or on a boundary, border or edge of the beam path. Further, calculating the first portion of the surface of the body part located inside the beam path may comprise determining a first subset of the surface data, which first subset of the surface data may be indicative and/or representative of the first portion of the surface of the body part located inside the beam path. In other words, the first portion of the surface may refer to and/or be represented by a first subset of the surface data as determined based on intersecting the surface and the beam path. Moreover, calculating the first portion may comprise determining an overlap of the surface with the beam path, wherein the overlap may refer to an overlap region and/or an overlap volume. Accordingly, the first portion of the surface may correlate with an overlap, an overlap region and/or an overlap volume of the body part and the beam path.

Apart from that, e.g. a volume covered and/or enclosed by the first portion of the surface may be determined. Hence, the first portion of the surface can provide a measure (e.g. a first measure) for the amount of surface and/or an amount of volume of the body part, which is at least partly enclosed by the first portion of the surface and which is arranged and/or located inside the beam path.

Alternatively or additionally to the first portion of the surface located inside the beam path, the second portion of the surface located outside the beam path can be calculated. Analogue to the first portion, also the second portion may refer to and/or be represented by a second subset of the surface data as determined based on intersecting the surface and the beam path. Accordingly, calculating the second portion of the surface of the body part located outside the beam path may comprise determining the second subset of the surface data, which second subset of the surface data may be indicative and/or representative of the second portion of the surface of the body part located outside the beam path. Therein, the term "located outside" may mean that the second portion is arranged outside of the volume covered by the radiation beam which is represented by the reconstructed beam path. Accordingly, the second portion of the surface can provide a measure for the amount of surface and/or amount of volume enclosed by this surface that is arranged and/or located outside the beam path.

Moreover, a volume covered and/or enclosed by the second portion of the surface may be determined based on intersecting the beam path and the surface. Hence, the second portion of the surface can provide a measure (e.g. a second measure) for the amount of surface and/or an amount of volume of the body part, which is at least partly enclosed by the second portion of the surface and which is arranged and/or located outside the beam path.

In this context, the first portion and/or the second portion of the surface may generally considered as an indicator for a quality of a current positioning of the patient for the radiation treatment.

The invention may be considered being based on the following insights and findings. In conventional approaches and methods of positioning the patient, usually a reference image of the patient and/or at least a part thereof is used, which represents a target position for the patient. At least a part of the surface of the patient can then be determined with a 3D surface scanner, which surface represents the current position of the patient. The reference image and the surface of the patient determined with the surface scanner can be displayed on a graphical user interface and the patient can be positioned such that at least a part of the reference image is aligned with at least a part of the surface as acquired with the surface scanner. Particularly since non-rigid body parts, such as the breast, can be deformed or displaced with respect to the reference image, such body parts can only hardly be positioned for the radiation treatment by means of this approach. To address this, in conventional methods, non-rigid body parts are either masked during the actual positioning or a deviation with respect to the reference image is determined and displayed on the user interface. Both conventional approaches, however, aim on positioning the patient or the body part thereof based on aligning a current surface of the patient captured with the surface scanner with a pre-recorded reference image. As rather large deformations or displacements of the non-rigid body parts, and hence large deviations of a current shape or form of the body part to the corresponding shape or form in the reference image, can occur, both conventional approaches may have certain deficits and may be error prone.

In contrast to the conventional approaches described hereinabove, according to the present invention the surface of the body part is intersected with the reconstructed beam path to determine the first portion of surface located inside the beam path and/or the second portion of the surface located outside the beam path. This allows to accurately position the patient and/or the body part with respect to the isocenter position and the volume that is covered by the radiation beam during the subsequent treatment, and not with respect to a reference image as used in conventional approaches, which reference image may not adequately reflect a current shape, form or position of the body part. Accordingly, the present invention allows to precisely position the patient and/or the body part with respect to the actual beam, thereby improving the overall effectivity of the treatment.

It is emphasized, that the invention solely relates to positioning the patient for radiation treatment and/or to monitoring a position of the patient during the radiation treatment. Accordingly, the invention does not involve or in particular comprise or encompass an invasive step which would represent a substantial physical interference with the body of the patient requiring professional medical expertise to be carried out and entailing a substantial health risk even when carried out with the required professional care and expertise. Particularly, the invention does not involve, comprise and/or encompass any surgical or therapeutic activity. The invention is instead directed as applicable to radiation treatment monitoring without carrying out the actual radiation treatment on the patient. For this reason alone, no surgical or therapeutic activity and in particular no surgical or therapeutic step is necessitated or implied by carrying out the invention.

According to an embodiment of the invention, the method further comprises segmenting the surface data, thereby determining and/or generating at least one target surface segment of the body part of the patient to be irradiated in the radiation treatment.

Therein, segmenting the surface data may comprise identifying at least a part of the surface of the body part in the surface data. Optionally, the identified surface of the body part may be labelled. Generally, the identified surface of the body part may refer to and/or may be part of the target surface segment of the body part. Accordingly, the target surface segment may refer to a subset of the surface data representing the surface of the body part or at least a part thereof. Therein, segmenting the surface data may comprise manually segmenting, e.g. by means of a user via a user interface, or automatically segmenting, e.g. by means of software and/or a segmentation algorithm, such as e.g. atlas segmentation or atlas registration, the surface data. Alternatively or additionally, surface changes may be determined based on processing a sequence of surface data, which surface changes may e.g. be caused by a breathing of the patient. Based on these surface changes, the target surface segment can be identified and the surface data can be segmented accordingly.

Segmenting the surface data and determining the target surface segment may allow to determine, compute and/or calculate numerical values of the surface of the body part located inside the beam path (i.e. the first portion of the surface) and/or numerical values of the surface of the body part located outside the beam path (i.e. the second portion of the surface). These numerical values may be absolute values or relative values, e.g. normalized to the total surface of the body part and/or the target surface segment. Apart from that, also numerical values of a volume enclosed at least partly by the first portion of the surface and/or enclosed at least partly by the second portion of the surface can be calculated. This allows to further optimize the positioning of the patient for the radiation treatment, particularly relative to the beam path.

According to an embodiment of the invention, calculating at least the first portion of the surface located inside the beam path and/or calculating at least the second portion of the surface located outside the beam path comprises:
  calculating a first measure of the at least one target surface segment, wherein the first measure is representative of, indicative of and/or correlates with an amount of surface and/or an amount of volume of the body part located inside the beam path; and/or
  calculating a second measure of the at least one target surface segment, wherein the second measure is representative of, indicative of and/or correlates with an amount of surface and/or an amount of volume of the body part located outside the beam path.

The first measure and/or the second measure can, for example, be determined, calculated and/or computed based on intersecting the target surface segment and the reconstructed beam path. Accordingly, the first measure may refer to and/or be indicative of at least a part of the target surface segment arranged inside the beam path. Based on this at least part of the surface target segment arranged inside the beam path, the amount of surface and/or the amount of volume of the body part arranged inside the beam path can be calculated. For instance, the volume of the body part arranged inside the beam path may be enclosed by the at least part of the target surface segment arranged inside the beam path and/or by at least a part of a boundary, border or edge of the reconstructed beam path. Accordingly, the amount of volume of the body part located inside the beam path can be calculated based on integrating over the at least part of the target surface segment arranged inside the beam path and/or over at least a part of the boundary, border or edge of the reconstructed beam path. Further, the amount of surface located inside the beam path may be calculated based on integrating over the part of the target surface segment that is arranged inside the beam path. In the context of the present disclosure, calculating the first measure may comprise determining the at least part of the target surface segment arranged inside the beam path, calculating the amount of surface arranged inside the beam path and/or calculating the amount of volume of the body part arranged inside the beam path.

The second measure may refer to at least a part of the target surface segment arranged outside the beam path. Accordingly, the second measure may refer to and/or be indicative of at least a part of the target surface segment arranged outside the beam path. Based on this at least part of the surface target segment arranged outside the beam path, the amount of surface and/or the amount of volume of the body part arranged outside the beam path can be calculated. For instance, the volume of the body part arranged outside the beam path may be enclosed by the at least part of the target surface segment arranged outside the beam path and/or by at least a part of a boundary, border or edge of the reconstructed beam path. Accordingly, the amount of volume of the body part located outside the beam path can be calculated based on integrating over the at least part of the target surface segment arranged outside the beam path and/or over at least a part of the boundary, border or edge of the reconstructed beam path. Further, the amount of surface located outside the beam path may be calculated based on integrating over the part of the target surface segment that is arranged outside the beam path. In the context of the present disclosure, calculating the second measure may comprise determining the at least part of the target surface segment arranged outside the beam path, calculating the amount of surface arranged outside the beam path and/or calculating the amount of volume of the body part arranged outside the beam path.

According to an embodiment of the invention, the method further comprises determining a first part of the at least one target surface segmented, which first part is located inside the beam path, and/or determining a second part of the at least one target surface segment, which second part is located outside the beam path.

Accordingly, the at least one target surface segment and/or the surface data of the body part to be irradiated may be segmented based on the reconstructed beam path into the first part of the at least one target surface segmented, which first part is located inside the beam path, and/or into the second part of the at least one target surface segment, which second part is located outside the beam path. In other words, the at least one target surface segment (and/or the surface data of the body part to be irradiated) may be intersected with the reconstructed beam path, thereby generating the first part of the at least one target surface segmented, which first part is located inside the beam path, and/or thereby generating the second part of the at least one target surface segment, which second part is located outside the beam path. Optionally, for the first part of the at least one target surface segment, the amount of surface and/or volume of the body part located inside the beam path may be calculated. Optionally, for the second part of the at least one target surface segment, the amount of surface and/or volume of the body part located outside the beam path may be calculated.

Further, the first part and/or the second part of the at least one target surface segment may be color-coded and/or displayed, e.g. on a graphical user interface. For instance, the first part of the target surface segment located inside the beam path may be colored and/or displayed in a first color and the second part of the target surface segment may be colored and/or displayed in a second color, which may differ from the first color.

According to an embodiment of the invention, the method further comprises positioning at least the body part of the patient, such that the first measure is maximized and/or the second measure is minimized.

The body part of the patient and/or the patient may e.g. be positioned based on moving and/or displacing a patient support unit and/or a or couch supporting at least a part of the patient. The patient support unit may be moved and/or displaced manually or automatically, such that the first measure is maximized and/or the second measure is minimized. By maximizing the first measure and/or by minimizing the second measure it may be ensured that as much tissue or volume of the body part to be irradiated as possible is irradiated with the radiation beam in the radiation treatment. Generally, this may improve an overall effectivity of the radiation treatment.

According to an embodiment of the invention, the method further a step of comparing the first measure and/or the second measure to at least one threshold value, wherein the at least one threshold value is indicative and/or representative of at least one of a minimum amount of surface of the body part located inside the beam path, a minimum amount of volume of the body part located inside the beam path, a maximum amount of surface of the body part located outside the beam path, a maximum amount of volume of the body part located outside the beam path, a ratio of an amount of surface of the body part located inside the beam path to an amount of surface of the body part located outside the beam path, and a ratio of an amount of volume of the body part located inside the beam path to an amount of volume of the body part located outside the beam path.

Generally, the at least one threshold value may refer to one or more boundary conditions which should be fulfilled in the radiation treatment. For instance, the at least one threshold value may denote a certain minimum percentage of the body part that should be irradiated in the radiation treatment. Hence, the patient should be positioned such that this minimum percentage is covered by the radiation beam during the actual radiation treatment. By comparing the first measure and/or the second measure to the one or more threshold values, the expected quality of the radiation treatment, when performed with the patient in the current position or posture, can be determined or estimated. Accordingly, by comparing the first measure and/or the second measure with the at least one threshold value, it can be determined whether the one or more boundary conditions, as specified by the one or more threshold values, are fulfilled for the current position or posture of the patient. This, in turn, allows to improve the positioning of the patient for the radiation treatment, such that the boundary conditions as specified by the one or more threshold values can be fulfilled.

According to an embodiment of the invention, the method further comprises a step of triggering, based on the comparison of the first measure and/or the second measure with the at least one threshold value, a beam-on signal to switch on the radiation beam or a beam-off signal to switch off the radiation beam.

Therein, triggering the beam-on signal and/or the beam-off signal may comprise generating the beam-on signal and/or the beam-off signal. Further, triggering the beam-on signal and/or the beam-off signal may comprise providing the beam-on signal and/or the beam-off signal to a medical system and/or a radiation treatment apparatus, which may switch on the radiation beam in response to receiving the beam-on signal and/or which may switch off the beam in response to receiving the beam-off signal. Generally, this may ensure that the radiation beam is only switched on if the comparison of the first measure and/or the second measure with the at least one threshold value indicates that the one or more boundary conditions for the radiation treatment, as specified by the one or more threshold values, are fulfilled. In other words, this may ensure that the radiation beam is only switched on if the patient and/or the body part to be irradiated is correctly positioned with respect to the beam path and/or with respect to the isocenter position. Accordingly, the overall radiation treatment may be improved.

According to an embodiment of the invention, the method further comprises a step of determining, based on the reconstructed beam path and based on segmenting the surface data, a further measure describing an amount of surface and/or an amount of volume of a further part of the patient, which is to be spared during the radiation treatment and which is located inside the beam path.

Generally, the further part of the patient that is to be spared during the radiation treatment may refer to healthy tissue of the patient, which preferably should not be irradiated during the radiation treatment and/or in which as little dose as possible should be deposited. Accordingly, by determining the further measure describing the amount of surface and/or volume of the further part of the patient arranged inside the beam path, it can be determined whether and how much healthy tissue of the patient would be irradiated in the current position or posture of the patient. This allows to position the patient and/or the body part of the patient, such that the further measure can be minimized. This way, a dose deposited in the healthy tissue can be reduced or even avoided, thereby further improving the quality of the radiation treatment.

According to an embodiment of the invention, at least the steps of
  providing surface data from the 3D surface scanner; and
  calculating at least the first portion of the surface of the body part located inside the beam path and/or at least the second portion of the surface of the body part located outside the beam path,
are repeated in an iteration process, wherein the method further comprises a step of deriving a breathing signal of the patient based on a sequence, e.g. a time sequence, of calculated first portions of the surface located inside the beam path and/or based on a sequence, e.g. a time sequence, of calculated second portions of the surface located outside the beam path.

Due to the breathing of the patient, the amount of surface and/or the amount of volume of the body part located inside the beam path and/or located outside the beam path may periodically vary. Accordingly, a time sequence or time series of first portions of the surface located inside the beam path and/or a time sequence or time series of second portions of the surface located outside the bam path may correlate with the actual breathing of the patient. Hence, the breathing signal of the patient can be derived from such a sequence of the first and/or second portions, wherein the breathing signal may comprise a breathing frequency, a breathing strength and/or a breathing amplitude of the patient.

According to an embodiment of the invention, the method further comprises displaying, on a graphical user interface, the reconstructed beam path and the surface of at least the body part of the patient. Displaying the reconstructed beam path and the surface of the body part may allow a user to visually inspect the current positioning or posture of the patient. Also, this may allow to intuitively correct and/or adjust the current positioning of the patient, e.g. by moving a patient support unit or a couch supporting at least a part of the patient.

According to an embodiment of the invention, the method further comprises color-coding, on the graphical user interface, the first portion of the surface located inside the beam path and the second portion of the surface located outside the beam path using different colors and/or using at least one coloring rule.

Generally, the first portion of the surface and the second portion of the surface may be color-coded in an arbitrary color. For instance, the first portion may be color-coded in green and the second portion may be color-coded in red. Also, a surface of a further part of the patient, which is to be spared in the radiation treatment, can be displayed and/or color-coded on the graphical user interface, wherein a color of the surface of this further part may differ from the color of the first portion and/or the second portion. A suitable coloring rule may e.g. comprise an information about a color in which the first portion is to be displayed or color-coded, an information about a color in which the second portion is to be displayed or color-coded and/or an information in which the surface of the further part that is to be spared in the radiation treatment is displayed or color-coded. Moreover, the first measure, the second measure and/or the further measure may be used for color-coding. In other, words, the color-coding may be based on any of the first measure, the second measure and the further measure. Generally, color-coding the first portion, the second portion and/or the surface of the further part of the patient, which is to be spared in the radiation treatment, may allow to graphically illustrate or visualize a quality of the current position or posture of the patient for the radiation treatment. Further, by means of the color-coding, guidance can be provided to a user (e.g. medical staff) on how to, in which direction and/or by what distance the couch or patient support unit supporting the patient is to be moved and/or displaced, such that the patient is correctly positioned for the radiation treatment. Overall, this may simplify and further improve the process of positioning the patient.

According to an embodiment of the invention, the beam path is reconstructed based on one or more of at least one beam parameter describing a direction of the radiation beam, at least one beam parameter describing a shape of the radiation beam, the isocenter position, a gantry angle of the radiation treatment apparatus, a distance between a treatment beam source of the radiation treatment apparatus and the isocenter position, an aperture configuration of the treatment beam source, an aperture angle of the treatment beam source, and a collimator configuration of a collimator of the radiation treatment apparatus. Alternatively or additionally, the planning data for the radiation treatment comprise one or more of at least one beam parameter describing a direction of the radiation beam, at least one beam parameter describing a shape of the radiation beam, the isocenter position, a gantry angle of the radiation treatment apparatus, a distance between a treatment beam source of the radiation treatment apparatus and the isocenter position, an aperture configuration of the treatment beam source, an aperture angle of the treatment beam source, and a collimator configuration of a collimator of the radiation treatment apparatus. Taking into account one or more of the parameters described above that describe the beam path or a geometry thereof, the beam path may be accurately and precisely determined and/or reconstructed.

According to an embodiment of the invention, the body part of the patient to be irradiated in the radiation treatment is at least one of at least a part of a breast of the patient, e.g. an entire breast of the patient, and at least a part of a heel bone of the patient, e.g. the entire heel bone. As described above, the present invention may be particularly advantageous for positioning the patient for breast or heel bone cancer therapy. Particularly, the present invention may be advantageously applied for deep inspiration breath-hold applications in breast cancer therapy. However, the present invention is not limited in this respect, but rather can be applied or used for positioning any other body part of the patient for radiation treatment.

According to an embodiment of the invention, the method further comprises superimposing and/or fusing, on a graphical user interface, the surface described by the surface data and a predetermined and/or pre-recorded surface of the body part of the patient, wherein the predetermined surface is extracted from a pre-treatment image of at least the body part of the patient. The pre-treatment image may, for instance, refer to an image of the surface of the patient recorded with the 3D surface scanner, an magnet resonance image, an X-ray image, a computed tomography, CT, image of the patient or any other image acquired with any other imaging modality. Superimposing the surface described by the surface data with the predetermined surface extracted from the pre-treatment image may allow to at least roughly bring the patient into the correct position or posture for the radiation treatment, thereby rendering the overall process of positioning more efficient.

According to an embodiment of the invention, the method further comprises:
providing calibration data for the 3D surface scanner, the calibration data being indicative of the relative position of the 3D surface scanner and the isocenter position of the radiation treatment apparatus; and/or
calibrating, based on calibration data indicative of the relative position of the 3D surface scanner and the isocenter position of the radiation treatment apparatus, raw surface data from the 3D surface scanner, thereby generating the surface data.

Therein, calibrating the raw surface data may comprise transforming the raw surface data into a coordinate system, in which the isocenter position is known. Generally, calibrating the raw surface data may allow to visualize and/or display the surface data relative to the isocenter position. As a consequence, this allows to precisely align and/or position the patient or at least the body part thereof with respect to the isocenter position.

According to an embodiment of the invention, providing the calibration data comprises scanning, with the 3D surface scanner, at least a part of a surface of a phantom, e.g. a surface scannable phantom, positioned at the isocenter position, and registering the scanned surface of the at least part of the phantom against model data describing a geometry of the at least part of the phantom. The model data may, for example, comprise computer-aided design, CAD, data and/or any other suitable model data. By scanning the phantom placed at isocenter position and registering the scanned surface against the model data, the relative position of the isocenter position and a position of the 3D surface scanner can be accurately determined. Accordingly, the calibration data may comprise an information or data about the relative position of the isocenter position and the position of the 3D surface scanner. Therein, the term registering the scanned surface against the model data may comprise mapping the scanned surface and the model data. This may further comprise determining a relative shift, a displacement and/or a rotation of the scanned surface with respect to the model data.

In a second aspect, the invention is directed to a program or computer program which, when running on at least one processor (for example, a processor) of at least one computer (for example, a computer) or when loaded into at least one memory (for example, a memory) of at least one computer (for example, a computer), causes the at least one computer to perform the above-described method according to the first aspect.

The invention may alternatively or additionally relate to a (physical, for example electrical, for example technically generated) signal wave, for example a digital signal wave, carrying information which represents the program, for example the aforementioned program, which for example comprises code means which are adapted to perform any or all of the steps of the method according to the first aspect. A computer program or program stored on a disc is a data file, and when the file is read out and transmitted it becomes a data stream for example in the form of a (physical, for example electrical, for example technically generated) signal. The signal can be implemented as the signal wave which is described herein. For example, the signal and/or the signal wave is constituted to be transmitted via a computer network, for example LAN, WLAN, WAN, for example the internet. The invention according to the second aspect therefore may alternatively or additionally relate to a data stream representative of the aforementioned program.

In a third aspect, the invention is directed to a non-transitory computer-readable program storage medium on which the program according to the second aspect is stored.

In a fourth aspect, the invention is directed to at least one computer (for example, a computer), comprising at least one processor (for example, a processor) and at least one memory (for example, a memory), wherein the program according to the second aspect is running on the processor or is loaded into the memory, and/or wherein the at least one computer comprises the computer-readable program storage medium according to the third aspect.

In a fifth aspect, the invention is directed to a medical system, comprising:
a) the at least one computer according to the fourth aspect;
b) at least one electronic data storage device storing at least the surface data and/or the planning data; and
c) a medical device for carrying out a medical procedure on the patient, such as e.g. the radiation treatment,
wherein the at least one computer is operably coupled to
the at least one electronic data storage device for acquiring and/or retrieving, from the at least one data storage device, at least the surface data and/or the planning data, and
the medical device for issuing a control signal to the medical device for controlling the operation of the medical device on the basis of the calculated first portion of the surface located inside the bam path and/or the calculated second portion of the surface located outside the beam path.

According to an embodiment of the invention, the medical system further comprises a 3D surface scanner for acquiring surface data of at least a part of the patient. Alternatively or additionally, the medical device comprises a radiation treatment apparatus comprising a treatment beam source and a patient support unit, such as e.g. a couch or any other patient support structure, wherein the at least one computer is operably coupled to the radiation treatment apparatus for issuing a control signal to the radiation treatment apparatus for controlling, on the basis of the calculated first portion of the surface located inside the beam path and/or on the basis of the calculated second portion of the surface located outside the beam path, at least one of an operation of the treatment beam source and a position of the patient support unit.

The present invention also relates to the use of any of the first to fifth aspect. Particularly, the invention also relates to the use of the method according to the first aspect, the program according to the second aspect, the computer-readable medium according to the third aspect and/or the computer according to the fourth aspect in the medical system or any embodiment thereof according to the fifth aspect.

Moreover, it is emphasized that features, functions, elements and/or steps, which are described above and in the following with reference to one aspect of the invention, equally apply to any other aspect of the invention described above and in the following. Particularly, features and/or steps, as described above and in the following with reference to the method according to the first aspect, equally apply the computer program according to the second aspect, to the computer-readable medium according to the third aspect, to the computer according to the fourth aspect and/or to the medical system according to the fifth aspect, and vice versa.

These and other aspects of the invention will be apparent from and elucidated with reference to the embodiments described hereinafter.

DEFINITIONS

In this section, definitions for specific terminology used in this disclosure are offered which also form part of the present disclosure.

Computer Implemented Method

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating or determining steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is a virtual reality device or an augmented reality device (also referred to as virtual reality glasses or augmented reality glasses) which can be used as "goggles" for navigating. A specific example of such augmented reality glasses is Google Glass (a trademark of Google, Inc.). An augmented reality device or a virtual reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. An example of such a digital lightbox is Buzz®, a product of Brainlab AG. The monitor may also be the monitor of a portable, for example handheld, device such as a smart phone or personal digital assistant or digital media player.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

Acquiring Data

According to the present disclosure, the terms acquiring data and retrieving data may be used synonymously. The expression "acquiring data" or "retrieving data" for example encompasses (within the framework of a computer implemented method) the scenario in which the data are determined by the computer implemented method or program. Determining data for example encompasses measuring physical quantities and transforming the measured values into data, for example digital data, and/or computing (and e.g. outputting) the data by means of a computer and for example within the framework of the method in accordance with the invention. The meaning of "acquiring data" also for example encompasses the scenario in which the data are received or retrieved by (e.g. input to) the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

Registering

The n-dimensional image of a body is registered when the spatial location of each point of an actual object within a space, for example a body part in an operating theatre, is assigned an image data point of an image (CT, MR, etc.) e.g. stored in a navigation system.

Image Registration

Image registration is the process of transforming different sets of data into one co-ordinate system. The data can be multiple photographs and/or data from different sensors, different times or different viewpoints. It is used in computer vision, medical imaging and in compiling and analysing images and data from satellites. Registration is necessary in order to be able to compare or integrate the data obtained from these different measurements.

Atlas/Atlas Segmentation

Preferably, atlas data is acquired which describes (for example defines, more particularly represents and/or is) a general three-dimensional shape of the anatomical body part. The atlas data therefore represents an atlas of the anatomical body part. An atlas typically consists of a plurality of generic models of objects, wherein the generic models of the objects together form a complex structure. For example, the atlas constitutes a statistical model of a patient's body (for example, a part of the body) which has been generated from anatomic information gathered from a plurality of human bodies, for example from medical image data containing images of such human bodies. In principle, the atlas data therefore represents the result of a statistical analysis of such medical image data for a plurality of human bodies. This result can be output as an image—the atlas data therefore contains or is comparable to medical image data. Such a comparison can be carried out for example by applying an image fusion algorithm which conducts an image fusion between the atlas data and the medical image data. The result of the comparison can be a measure of similarity between the atlas data and the medical image data. The atlas data comprises image information (for example, positional image information) which can be matched (for example by applying an elastic or rigid image fusion algorithm) for example to image information (for example, positional image information) contained in medical image data so as to for example compare the atlas data to the medical image data in order to determine the position of anatomical structures in the medical image data which correspond to anatomical structures defined by the atlas data.

The human bodies, the anatomy of which serves as an input for generating the atlas data, advantageously share a common feature such as at least one of gender, age, ethnicity, body measurements (e.g. size and/or mass) and pathologic state. The anatomic information describes for example the anatomy of the human bodies and is extracted for example from medical image information about the human bodies. The atlas of a femur, for example, can comprise the head, the neck, the body, the greater trochanter, the lesser trochanter and the lower extremity as objects which together make up the complete structure. The atlas of a brain, for example, can comprise the telencephalon, the cerebellum, the diencephalon, the pons, the mesencephalon and the medulla as the objects which together make up the complex structure. One application of such an atlas is in the segmentation of medical images, in which the atlas is matched to medical image data, and the image data are compared with the matched atlas in order to assign a point (a pixel or voxel) of the image data to an object of the matched atlas, thereby segmenting the image data into objects.

Treatment Beam

The present invention relates to the field of controlling a treatment beam. The treatment beam treats body parts which are to be treated and which are referred to in the following as "treatment body parts" or "body parts". These body parts are for example parts of a patient's body, i.e. anatomical body parts.

The present invention relates to the field of medicine and for example to the use of beams, such as radiation beams, to treat parts of a patient's body, which are therefore also referred to as treatment beams. A treatment beam treats body parts which are to be treated and which are referred to in the following as "body parts". These body parts are for example parts of a patient's body, i.e. anatomical body parts. Ionising radiation is for example used for the purpose of treatment. For example, the treatment beam comprises or consists of ionising radiation. The ionising radiation comprises or consists of particles (for example, sub-atomic particles or ions) or electromagnetic waves which are energetic enough to detach electrons from atoms or molecules and so ionise them. Examples of such ionising radiation include x-rays, high-energy particles (high-energy particle beams) and/or ionising radiation emitted from a radioactive element. The treatment radiation, for example the treatment beam, is for example used in radiation therapy or radiotherapy, such as in the field of oncology. For treating cancer in particular, parts of the body comprising a pathological structure or tissue such as a tumour are treated using ionising radiation. The tumour is then an example of a treatment body part.

The treatment beam is preferably controlled such that it passes through the treatment body part or body part. However, the treatment beam can have a negative effect on body parts outside the treatment body part. These body parts may also be referred to here as "outside body parts".

Arrangement of Treatment Beams

A treatment body part or body part can be treated by one or more treatment beams issued from one or more directions at one or more times. The treatment by means of the at least one treatment beam thus follows a particular spatial and temporal pattern. The term "beam arrangement" is then used to cover the spatial and temporal features of the treatment by means of the at least one treatment beam. The beam arrangement is an arrangement of at least one treatment beam.

The "beam positions" or "beam paths" describe the positions of the treatment beams of the beam arrangement. The arrangement of beam positions is referred to as the positional arrangement. A beam position or beam path is preferably defined by the beam direction and additional information which allows a specific location, for example in three-dimensional space, to be assigned to the treatment beam, for example information about its co-ordinates in a defined co-ordinate system. The specific location is a point, preferably a point on a straight line. This line is then referred to as a "beam line" and extends in the beam direction, for example along the central axis of the treatment beam. The defined co-ordinate system is preferably defined relative to the treatment device, e.g. to the isocenter position, or relative to at least a part of the patient's body. The positional arrangement comprises and for example consists of at least one beam path, at least one beam position, for example a discrete set of beam positions (for example, two or more different beam positions), or a continuous multiplicity (manifold) of beam positions.

For example, one or more treatment beams adopt(s) the treatment beam position(s) or beam paths defined by the positional arrangement simultaneously or sequentially during treatment (for example sequentially if there is only one beam source to emit a treatment beam). If there are several beam sources, it is also possible for at least a subset of the beam positions or beam paths to be adopted simultaneously by treatment beams during the treatment. For example, one or more subsets of the treatment beams can adopt the beam positions or beam paths of the positional arrangement in accordance with a predefined sequence. A subset of treatment beams comprises one or more treatment beams. The complete set of treatment beams which comprises one or more treatment beams which adopt(s) all the beam positions defined by the positional arrangement is then the beam arrangement.

Elastic Fusion, Image Fusion/Morphing, Rigid Image Fusion

Image fusion can be elastic image fusion or rigid image fusion. In the case of rigid image fusion, the relative position between the pixels of a 2D image and/or voxels of a 3D image is fixed, while in the case of elastic image fusion, the relative positions are allowed to change.

In this application, the term "image morphing" is also used as an alternative to the term "elastic image fusion", but with the same meaning.

Elastic fusion transformations (for example, elastic image fusion transformations) are for example designed to enable a seamless transition from one dataset (for example a first dataset such as for example a first image) to another dataset (for example a second dataset such as for example a second image). The transformation is for example designed such that one of the first and second datasets (images) is deformed, for example in such a way that corresponding structures (for example, corresponding image elements) are arranged at the same position as in the other of the first and second images. The deformed (transformed) image which is transformed from one of the first and second images is for example as similar as possible to the other of the first and second images. Preferably, (numerical) optimisation algorithms are applied in order to find the transformation which results in an optimum degree of similarity. The degree of similarity is preferably measured by way of a measure of similarity (also referred to in the following as a "similarity measure"). The parameters of the optimisation algorithm are for example vectors of a deformation field. These vectors are determined by the optimisation algorithm in such a way as to result in an optimum degree of similarity. Thus, the optimum degree of similarity represents a condition, for example a constraint, for the optimisation algorithm. The bases of the vectors lie for example at voxel positions of one of the first and second images which is to be transformed, and the tips of the vectors lie at the corresponding voxel positions in the transformed image. A plurality of these vectors is preferably provided, for instance more than twenty or a hundred or a thousand or ten thousand, etc. Preferably, there are (other) constraints on the transformation (deformation), for example in order to avoid pathological deformations (for instance, all the voxels being shifted to the same position by the transformation). These constraints include for example the constraint that the transformation is regular, which for example means that a Jacobian determinant calculated from a matrix of the deformation field (for example, the vector field) is larger than zero, and also the constraint that the transformed (deformed) image is not self-intersecting and for example that the transformed (deformed) image does not comprise faults and/or ruptures. The constraints include for example the constraint that if a regular grid is transformed simultaneously with the image and in a corresponding manner, the grid is not allowed to interfold at any of its locations. The optimising problem is for example solved iteratively, for example by means of an optimisation algorithm which is for example a first-order optimisation algorithm, such as a gradient descent algorithm. Other examples of optimisation algorithms include optimisation algorithms which do not use derivations, such as the downhill simplex algorithm, or algorithms which use higher-order derivatives such as Newton-like algorithms. The optimisation algorithm preferably performs a local optimisation. If there is a plurality of local optima, global algorithms such as simulated annealing or generic algorithms can be used. In the case of linear optimisation problems, the simplex method can for instance be used.

In the steps of the optimisation algorithms, the voxels are for example shifted by a magnitude in a direction such that the degree of similarity is increased. This magnitude is preferably less than a predefined limit, for instance less than one tenth or one hundredth or one thousandth of the diameter of the image, and for example about equal to or less than the distance between neighbouring voxels. Large deformations can be implemented, for example due to a high number of (iteration) steps.

The determined elastic fusion transformation can for example be used to determine a degree of similarity (or similarity measure, see above) between the first and second datasets (first and second images). To this end, the deviation between the elastic fusion transformation and an identity transformation is determined. The degree of deviation can for instance be calculated by determining the difference between the determinant of the elastic fusion transformation and the identity transformation. The higher the deviation, the lower the similarity, hence the degree of deviation can be used to determine a measure of similarity.

A measure of similarity can for example be determined on the basis of a determined correlation between the first and second datasets.

BRIEF DESCRIPTION OF THE DRAWINGS

In the following, the invention is described with reference to the appended figures which give background explanations and represent specific embodiments of the invention. The scope of the invention is however not limited to the specific features disclosed in the context of the figures, wherein.

The figures are schematic only and not true to scale. In principle, identical or like parts, elements and/or steps are provided with identical or like reference symbols in the figures.

DESCRIPTION OF EMBODIMENTS

Figure 1:
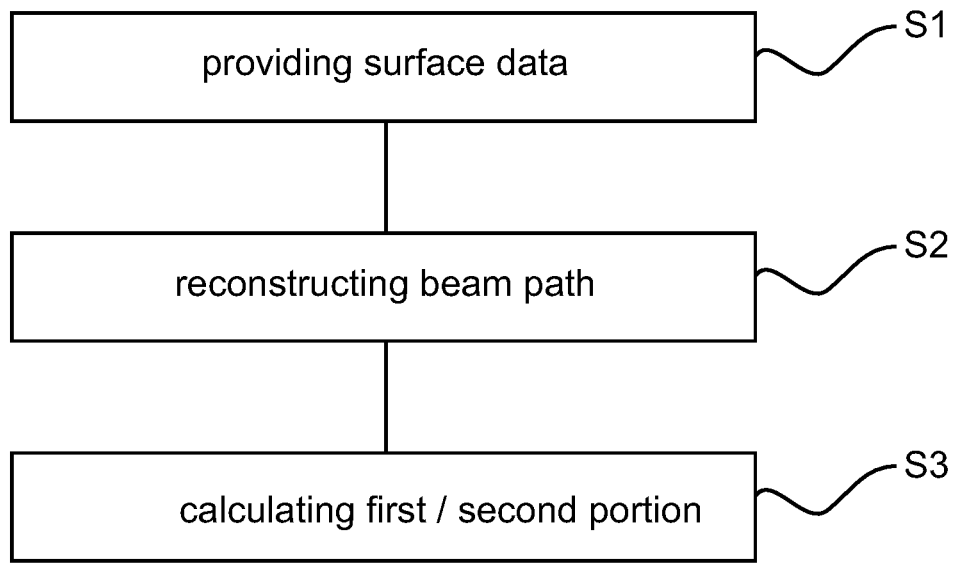
FIG. 1 shows a flowchart illustrating steps of a method of positioning a patient for radiation treatment and/or of monitoring a position of the patient during the radiation treatment according to an exemplary embodiment of the invention.

FIG. 1 shows a flowchart illustrating steps of a method of positioning a patient for radiation treatment and/or of monitoring a position of the patient during the radiation treatment according to an exemplary embodiment of the invention.

Figure 2A:
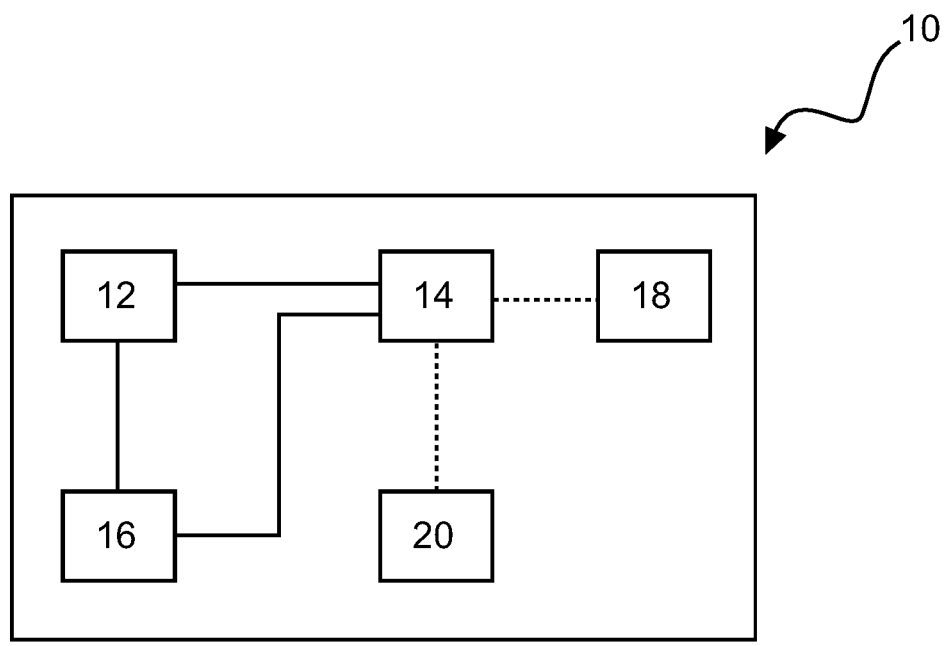
FIG. 2A schematically shows a medical system according to an exemplary embodiment of the invention.
Figure 2B:
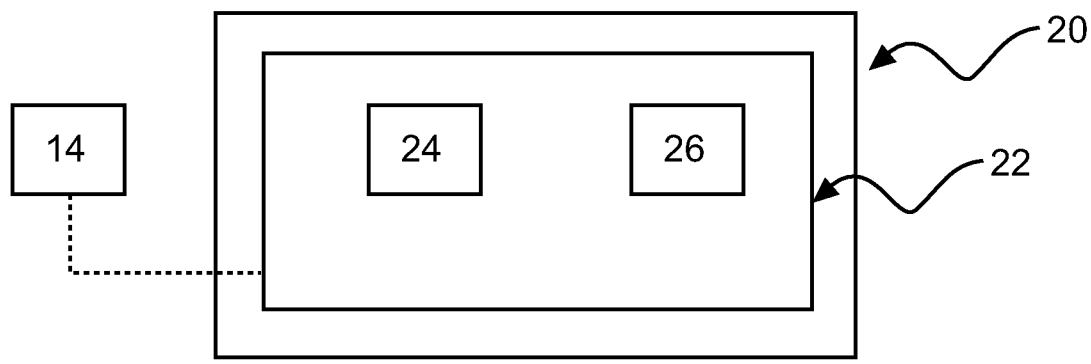
FIG. 2B schematically shows a medical device of the medical system of FIG. 2A.

Step S1 comprises providing surface data from a 3D surface scanner 12 (see FIGS. 2A and 2B), wherein the surface data are indicative of a surface of at least a part of a body part of the patient to be irradiated in the radiation treatment, and wherein the surface data are calibrated with respect to a relative position of the 3D surface scanner and an isocenter position of a radiation treatment apparatus 22 (see FIGS. 2A and 2B). Accordingly, the surface data may be given relative to the isocenter position and/or in a coordinate system, in which the isocenter position is known. The surface data may be provided, e.g. to a computer 14 (see FIGS. 2A and 2B), by the 3D surface scanner 12 directly or via a data storage device 16 (see FIGS. 2A and 2B), as described in more detail with reference to FIGS. 2A and 2B.

Step S2 comprises reconstructing a beam path of a radiation beam based on planning data for the radiation treatment. The planning data may e.g. be stored on the data storage device as described with reference to FIGS. 2A and 2B. The planning data may be retrieved from the data storage device, e.g. by the computer and/or processed by the computer to derive the beam path. Therein, the planning data may comprise one or more of at least one beam parameter describing a direction of the radiation beam, at least one beam parameter describing a shape of the radiation beam, the isocenter position, a gantry angle of the radiation treatment apparatus, a distance between a treatment beam source of the radiation treatment apparatus and the isocenter position, an aperture configuration of the treatment beam source, an aperture angle of the treatment beam source, and a collimator configuration of a collimator of the radiation treatment apparatus.

Step S3 comprises calculating, based on intersecting the surface described by the surface data and the reconstructed beam path, at least a first portion of the surface of the body part located inside the beam path and/or at least a second portion of the surface of the body part located outside the beam path, as will be further discussed in the following figures.

By determining the first portion and/or the second portion, the relative position of the body part and the beam path, which is indicative of a volume covered by the actual radiation or treatment beam during the radiation treatment, can be determined. This, in turn, allows to determine whether the patient is correctly positioned or whether the patient should be moved and/or displaced for the actual radiation treatment.

It is to be noted that based on intersecting the beam path and the surface of the patient, the first portion of the surface and/or the second portion of the surface can be segmented. Accordingly, the first portion of the surface may denote a first surface segment and the second portion may denote a second surface segment, as will be further discussed hereinafter.

FIG. 2A shows schematically a medical system 10 according to an exemplary embodiment of the invention and/or according to the fifth aspect. The system is in its entirety identified by reference numeral 10 and comprises a 3D surface scanner 12 for acquiring surface data of at least a part of a patient. The surface scanner 12 may comprise one or more sensors, such as e.g. one or more cameras, at least one 3D camera, at least one stereo camera, at least one distance sensor, at least one laser distance sensor, at least one LIDAR sensor, and/or any other suitable sensor.

The medical system 10 further comprises a computer 14, an electronic data storage device (such as a hard disc) 16 for storing at least surface data of the 3D surface scanner and/or planning data for the radiation treatment. The computer 14 may be coupled to one or both of the storage device 16 and the surface scanner 12 in order to retrieve and/or process the surface data and/or the planning data.

The medical system 10 further comprises a graphical user interface 18. On the user interface 18, e.g. the surface of at least a part of the patient as described by the surface data and/or the reconstructed beam path can be displayed and/or visualized.

The medical system 10 further comprises a medical device 20, e.g. for carrying out a medical procedure, particularly for performing the radiation treatment. The components of the medical system 10 have the functionalities and properties explained above and in the following with regard to the fifth and/or any other aspect of the present disclosure.

Particularly, the at least one computer 14 is operably coupled to the at least one electronic data storage 16 device for acquiring, from the at least one data storage device 16, at least the surface data and/or the planning data. Further, computer 14 is coupled to the graphical user interface 18. Moreover, the computer 14 is coupled to the medical device 20 for issuing a control signal to the medical device 20 for controlling the operation of the medical device 20, e.g. on the basis of the first portion of the surface located inside the beam path and/or on the basis of the second portion of the surface located outside the beam path.

FIG. 2B schematically shows a medical device 20 of the medical system 10 of FIG. 2A. The medical device 20 comprises a radiation treatment apparatus 22 comprising a treatment beam source 24 and a patient support unit 26, wherein the at least one computer 20 is operably coupled to the radiation treatment apparatus 22 for issuing a control signal to the radiation treatment apparatus 22 for controlling, on the basis of the first portion of the surface located inside the beam path and/or on the basis of the second portion of the surface located outside the beam path, at least one of the operation of the treatment beam source 24 and the position of the patient support unit 26. In other words, the computer can at least partly control the radiation treatment apparatus 22, the treatment beam source 24 and/or the patient support unit 26. By way of example, the computer 14 may generate and/or provide a beam-on signal to the treatment beam source 24 to switch the radiation beam on. Alternatively or additionally, the computer 14 may generate and/or provide a beam-off signal to switch the radiation beam off. Moreover, the computer 14 may generate and/or provide one or more control signals to control the position of the patient support unit 26.

Figure 3A:
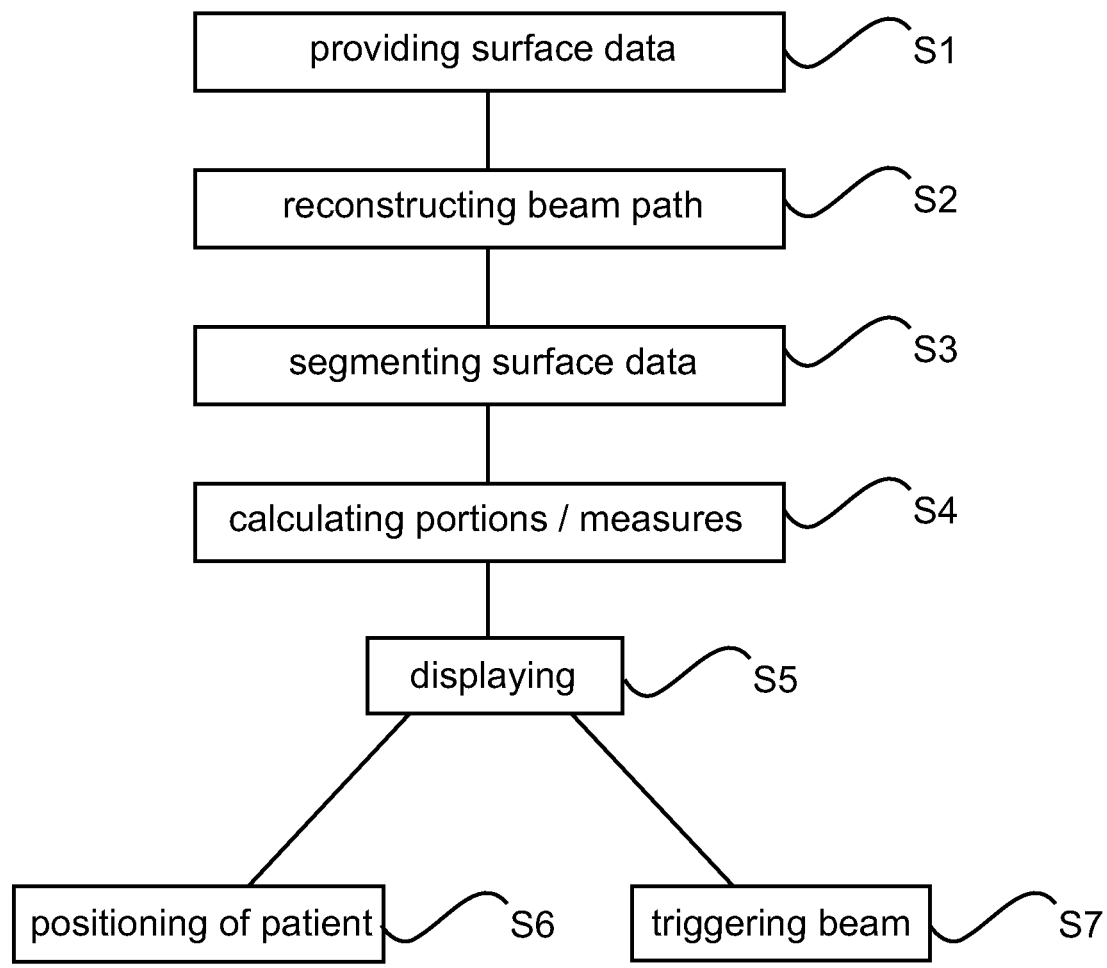
FIG. 3A shows a flowchart illustrating steps of a method of positioning a patient for radiation treatment and/or of monitoring a position of the patient during the radiation treatment according to an exemplary embodiment of the invention.
Figure 3B:
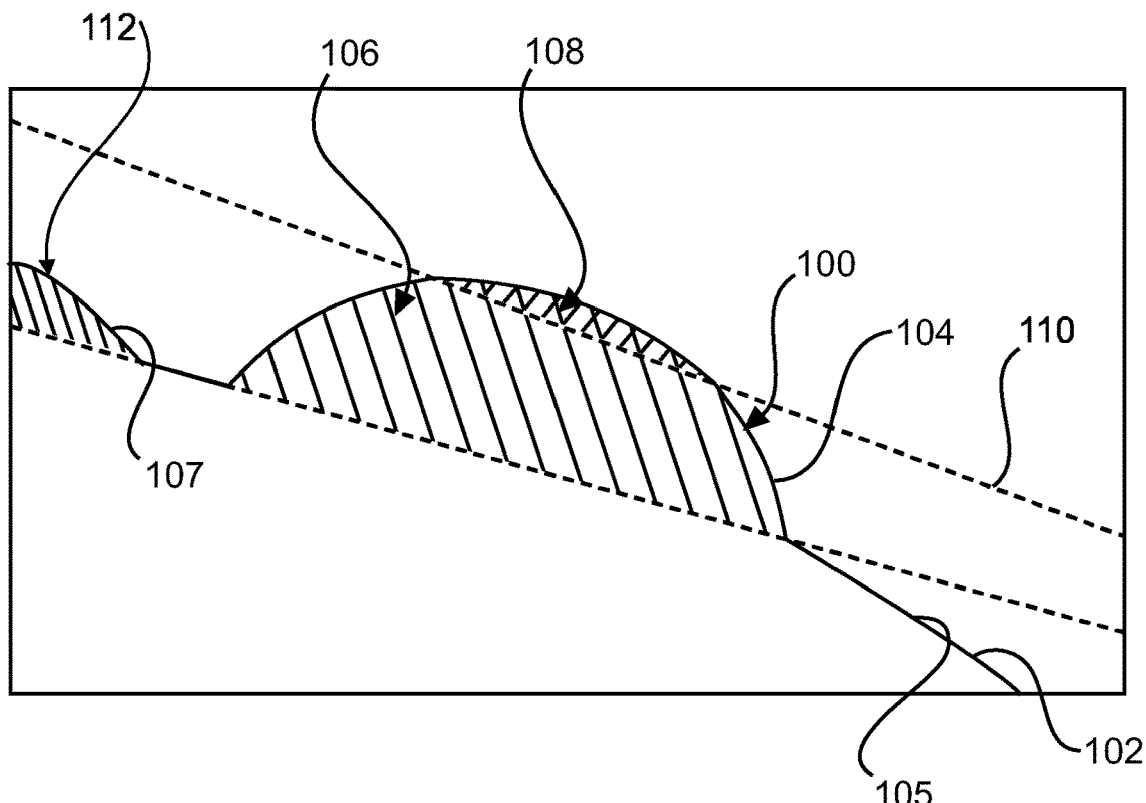
FIG. 3B shows a surface of a patient and a reconstructed beam path to illustrate steps of the method of FIG. 3A.

FIG. 3A shows a flowchart illustrating steps of a method of positioning a patient for radiation treatment and/or of monitoring a position of the patient during the radiation treatment according to an exemplary embodiment of the invention irradiation. If not stated otherwise, the method described with reference to FIG. 3A comprises the same steps as the method described with reference to FIG. 1. FIG. 3B shows a surface 102 of a patient and a reconstructed beam path 102 to illustrate steps of the method of FIG. 3A. Particularly, FIG. 3B shows a surface 102, 104 of a body part 100 to be irradiated in the radiation treatment and the reconstructed beam path 102.

As described with reference to FIG. 1, step S1 comprises providing surface data from a 3D surface scanner 12. The surface data may be provided by the surface scanner 12 directly to the computer 14 or via the data storage device 16. The surface data are provided relative to the isocenter position, i.e. they are calibrated to the isocenter position, and/or they may be given in a specific coordinate system, in which the isocenter position is known. Alternatively, raw surface data may be calibrated by means of calibration data to provide the calibrated surface data. The calibration data may be indicative of a relative position of the surface scanner 12 and the isocenter position. Also the calibration data may be stored on the data storage device 16. For instance, the computer 14 may process the raw surface data and transform the raw surface data to the calibrated surface data based on the calibration data.

The surface data describe a surface 102 of at least a part of the patient, particularly of at least a part of the body part 100 to be irradiated in the radiation treatment. In the example shown in FIGS. 3A and 3B, the body part 100 is a breast 100 of a patient, as illustrated in FIG. 3B. The surface 102 of the body part 100 may be derived from the surface data, e.g. based on processing the surface data, interpolating the surface data, fitting the surface data or the like.

Optionally and/or in an optional step, the calibration data may be generated. For this purpose, e.g. at least a part of a phantom placed at isocenter position can be scanned with the surface scanner 12 and registered against and/or mapped to model data of the phantom describing a geometry of at least a part of the phantom, such as e.g. CAD data. This can, for instance, be done by means of the computer 14.

Step S2 comprises reconstructing a beam path 110 of a radiation beam based on planning data for the radiation treatment, as described with reference to FIG. 1. For this purpose, the computer 14 may retrieve and/or process the planning data from the data storage 16 and derive the beam path 110 from at least a part of the planning data. The beam path 110 may be reconstructed three-dimensionally. Particularly, the beam path 110 may be reconstructed relative to the isocenter position. Alternatively or additionally, the beam path 110 may be reconstructed in the same coordinate system as the (calibrated) surface data.

Step S3 comprises segmenting the surface data, thereby generating a target surface segment 104 of the body part to be irradiated in the radiation treatment. Accordingly, the surface 102 may be segmented in step S3 based on the body part 100. As illustrated in FIG. 3B, the target surface segment 104 may refer to a part of the patient's surface 102 that at least partly encompasses or surrounds the body part 100. In other words, the target surface segment 104 may refer to the surface 102 of the body part 100 that is to be irradiated. Optionally, one or more further surface segments 105, 107 of further parts of the patient can be generated and/or determined in step S3, wherein segments 105, 107 may refer to parts or portions of the patient which should preferably be spared in the radiation treatment.

Step S4 comprises calculating, based on intersecting the surface 102 described by the surface data and the reconstructed beam path 110, at least a first portion 106 of the surface 102 of the body part 110 and/or at least a first portion 106 of the target surface segment 104 located inside the beam path 110. Alternatively or additionally, in step S4 at least a second portion 108 of the surface 102 of the body part 110 and/or a second portion 108 of the target surface segment 104 located outside the beam path 110 can be calculated. Therein, the first portion 106 may be calculated based on determining a first subset of the surface data that describes the surface 102 of the body part 100 inside the beam path 110. Likewise, the second portion 108 may be calculated based on determining a second subset of the surface data that describes the surface 102 of the body part located outside the beam path 110.

Further, based on intersecting the beam path 110 and the surface 102 of the patient, the first portion 106 of the surface 102 and/or the second portion 108 of the surface 102 can be segmented, e.g. in step S4. Accordingly, the first portion 106 of the surface 102 may denote a first surface segment 106 and the second portion 108 may denote a second surface segment 108.

Alternatively or additionally to the first portion 106, a first measure of the target surface segment 104 can be calculated in step S4, wherein the first measure correlates with an amount of surface and/or an amount of volume of the body part 100 located inside the beam path 110. Accordingly, in step S4 the amount of surface of the body part 100 and/or the amount of volume of the body part 100 located inside the beam path 110 can be calculated. For determining the amount of surface, a surface value of the portion of the target surface segment 104 arranged inside the beam path 110 can be computed, e.g. based on integrating over this portion of the target surface segment 104. For determining the amount of volume, the volume enclosed by the portion of the target surface segment 104 inside the beam path 110 and/or by at least one boundary, edge or border of the beam path 110 can be computed, e.g. based on integrating over this volume.

Alternatively or additionally to the second portion 108, a second measure of the target surface segment 104 can be calculated in step S4, wherein the second measure correlates with an amount of surface and/or an amount of volume of the body part 100 located outside the beam path 110. Accordingly, in step S4 the amount of surface of the body part 100 and/or the amount of volume of the body part 100 located outside the beam path 110 can be calculated. For determining the amount of surface, a surface value of the portion of the target surface segment 104 arranged outside the beam path 110 can be computed, e.g. based on integrating over this portion of the target surface segment 104. For determining the amount of volume, the volume enclosed by the portion of the target surface segment 104 outside the beam path 110 and/or by at least one boundary, edge or border of the beam path 110 can be computed, e.g. based on integrating over this volume.

Optionally, in step S4 a further measure can be calculated based on the reconstructed beam path 110 and based on segmentation of the surface 102, such as e.g. based on the one or more surface segments 105, 107 determined in step S3. This further measure can describe and/or correlate with an amount of surface and/or an amount of volume of a part 113 of the patient that is to be spared in the radiation treatment. This part 113 of the patient may e.g. refer to healthy tissue that should preferably not be irradiated. For determining the amount of surface, a surface value of at least a portion of the surface segment 107 of the part 113 of the patient which is arranged inside the beam path 110 can be computed, e.g. based on integrating over this portion of the surface segment 107. For determining the amount of volume, the volume enclosed by the portion of the surface segment 106 inside the beam path 110 and/or by at least one boundary, edge or border of the beam path 110 can be computed, e.g. based on integrating over this volume. A similar measure can be computed for the other surface segment 105 or for any other surface segment potentially generated in step S3.

In an optional step S5 the reconstructed beam path 110 and surface 102 of at least a part of the patient are displayed, e.g. on the graphical user interface 18, as illustrated in FIG. 3B.

To illustrate the first portion 106, the second portion 108, the respective portions 106, 108 can be color-coded on the graphical user interface 18 using different colors for the first and second portion 106, 108, respectively. Color-coding can also be done based on at least one coloring rule. For this purpose, the first and/or second measure may be used as input for a coloring algorithm that applies the at least one coloring rule and determines a color for the first and/or second portion 106, 108, in which these portions 106, 108 are displayed on the user interface 18. Optionally, also the part 113 of the patient or the corresponding surface segment 107 of the part 113, which is to be spared, can be color coded.

Color-coding and displaying the first portion 106 and/or the second portion 108 can provide an estimate for a user about a correctness or quality of the current position of the patient for the radiation treatment. Also, guidance and/or instructions can be provided to the user by the color-coding, e.g. instructing the user to correctly position the patient. Such instructions may, for instance, comprise indications about where, in which direction and/or by what distance the patient support unit 26 is to be moved to correctly position the patient.

Optional step S6 comprises positioning the patient, e.g. based on moving and/or displacing the patient support unit 26, such that the first measure is maximized and/or the second measure is minimized. Optionally, the patient may also be positioned such that the further measure is minimized in step S6. Therein, the positioning of the patient may be performed automatically. For instance, the computer 14 may determine a movement of the patient support unit 26 appropriate for maximizing the first measure, minimizing the second measure and/or minimizing the further measure. The computer 14 may instruct the patient support unit 26 to move by providing at least one control signal indicative of the determined movement. Alternatively or additionally, the patient support unit 26 may be moved manually, e.g. by the user.

Optional step S7 comprises triggering (and/or generating) a beam-on signal to switch the radiation beam on and/or triggering (and/or generating) a beam-off signal to switch the radiation beam off. For generating the beam-on signal and/or the beam-off signal, the first measure and/or the second measure can be compared in step S7 to at least one threshold value. Therein, the at least one threshold value is indicative of at least one of a minimum amount of surface of the body part located inside the beam path, a minimum amount of volume of the body part located inside the beam path, a maximum amount of surface of the body part located outside the beam path, a maximum amount of volume of the body part located outside the beam path, a ratio of an amount of surface of the body part located inside the beam path to an amount of surface of the body part located outside the beam path, and a ratio of an amount of volume of the body part located inside the beam path to an amount of volume of the body part located outside the beam path. Alternatively or additionally, the at least one threshold value can be indicative of a maximum or minimum amount of surface (and/or amount of volume) of the part 113 of the patient (that is to be spared) located inside the beam path 110.

The beam-on signal and/or the beam-off signal may be triggered and/or generated by the computer 14 and provided to the treatment beam source 24 to switch the radiation beam on or off. This may ensure, that the beam is only switched on when the thresholds are met, e.g. when a maximum amount of surface (and/or volume) of the body part 100 to be irradiated is located inside the beam path 110, a minimum amount of surface (and/or volume) of the body part 100 to be irradiated is located outside the beam path 110 and/or a minimum amount of surface (and/or volume) of the part 113 of the patient to be spared is located inside the beam path 110.

Accordingly, the method described above allows to efficiently, reliably and precisely position the patient for the radiation treatment. Also, at least parts of the medical system 100 can be automatically controlled to ensure effectiveness of the radiation treatment while also reducing a dose deposited e.g. in healthy tissue. Hence, the overall radiation treatment can be significantly improved.

It is to be noted that step S7 can be performed subsequent to step S6. Alternatively, step S6 can be performed without performing step S7 and vice versa.

Further, it is to be noted that at least a part of the steps of the method of FIGS. 3A and 3B can be repeated in an iteration process. This may allow to monitor the radiation treatment in real-time.

Further, e.g. steps S1, S2 and S4 can be repeated, and a breathing signal of the patient can be derived from a sequence of calculated first portions, first measures, second portions, and/or second measures. Also the further measure can be used to derive the breathing signal of the patient.

Moreover, in an optional further step, the surface 102 described by the surface data, the target surface segment 104 and/or the one or more further surface segments 105, 107 can be superimposed and/or fused on the graphical user interface 18 with a predetermined surface of the body part 100 of the patient. Therein, the predetermined surface can be extracted and/or derived from a pre-treatment image of the body part 100 of the patient, e.g. from pre-recorded surface, from a pre-recorded CT scan, or any other pre-recorded image of the patient. The pre-determined surface may be located and/or arranged at a target position, in which the patient expectedly should be for the radiation treatment. The patient can then be moved, e.g. by moving the patient support unit 26, such that the surface 102 or at least a part thereof is aligned with the predetermined surface. This allows to at least roughly or grossly bring the patient into the correct position for the radiation treatment. To further position the patient at the correct position, to monitor its position and/or to monitor the radiation treatment, steps S1 to S7 can be performed.

Figure 4:
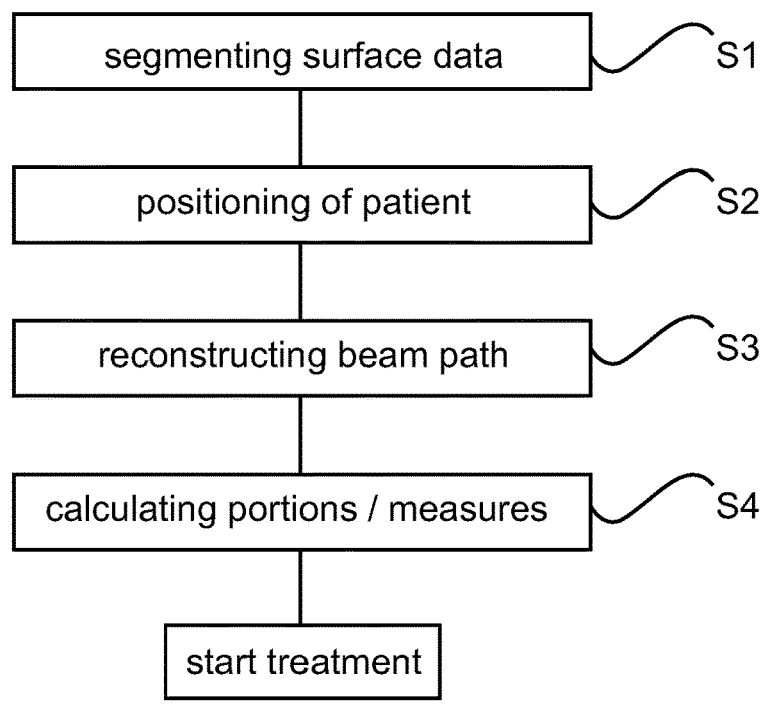
FIG. 4 shows a flowchart illustrating steps of a method of positioning a patient for radiation treatment according to an exemplary embodiment of the invention.

FIG. 4 shows a flowchart illustrating steps of a method of positioning a patient for radiation treatment according to an exemplary embodiment of the invention. If not stated otherwise, the method described with reference to FIG. 4 comprises the same steps as the methods described with reference to FIGS. 1, 3A, and 3B.

In the embodiment illustrated in FIG. 4, the 3D surface scanner 12 is calibrated to isocenter or isocenter position. In a step S1, the surface data or at least a part thereof is segmented to generate at least the target surface segment 104 of the body part 100 of the patient (see FIG. 3B). The segmentation may be done automatically or manually. Exemplary, the body part 100 can be a breast 100 and the target surface segment 104 may represent a breast segment 104 on the patient's surface 102. For instance, the surface data or calibrated surface data of the 3D surface scanner 12 can be used as input, e.g. for the computer 14 and/or an appropriate segmentation algorithm. The output can be one or more segmented parts or segments 104, 105, 107 of the patient's surface 102.

In an optional step S2, the surface 102 can be superimposed and/or fused with a predetermined surface, such as e.g. a surface of a part of the patient of a pre-recorded or pre-operative CT scan, which may e.g. show a part of the patient correctly positioned with respect to the isocenter position. Accordingly, aligning the surface 102, e.g. by moving the patient with the patient support unit 26, with the predetermined surface of the CT scan allows to at least grossly bring the patient into isocenter position and/or into the target position. In other words, the patient support unit 26 can be moved such that the patient is at least roughly in the target position with respect to the isocenter position. The surface data of the surface scanner 12 and the predetermined surface extracted from the CT scan can be used as input in step S2. Both the surface 102 as described by the surface data and the predetermined surface of the CT scan can be visualized on the graphical user interface 18. This may provide guidance to the user or operator on where to move the patient, e.g. in which direction and/or by what distance, to position the patient with respect to the isocenter position. It is to be noted, that the patient may also be automatically moved.

Step S3 comprises reconstructing the beam path 110 based on the planning data, as described with reference to previous figures. Therein, the beam path 110 may be reconstructed relative to the isocenter position, such that the surface data of the surface scanner 12, the (segmented) surface 102 described by the surface data and the beam path 110 can be analysed in a common coordinate system, in which the isocenter position is known. Further, in step S3 the surface 102 or segmented surface 102, particularly the target surface segment 104 and optionally the further surface segments 105, 107 are intersected with the beam path 110. As input for this step, the (segmented) surface 102 and/or surface segments 104, 105, 107 from step S1 as well as geometric information about the beam path 110, e.g. derived from the planning data, can be used. Optionally, also calibration data of the surface scanner 12 can be used as input in step S3, particularly if the surface data of the surface scanner 12 were not calibrated to iscenter position beforehand.

Step S4 comprises calculating at least one of the first portion 106 of the surface 102, 104 of the body part 100 located inside the beam path 110 or frustum 110, the first measure of the target surface segment 104, the second portion 108 of the surface 102, 104 of the body part 100 located outside the beam path 110 or frustum, and the second measure of the target surface segment 104, as described with reference to previous figures. Optionally, also the further measure of the part 113 of the patient that is located inside the beam path 110 or frustum 110 can be calculated. Accordingly, in step S4 it may be determined how much of the tissue of the body part 100 is located inside the beam path 110, how much tissue of the body part 100 is not located inside the beam path 110, and/or how much of healthy tissue 113 of the patient that is to be spared in the radiation treatment is located inside the beam path 110. In step S4, corresponding amounts of surface and/or volume can be output as numerical values, i.e. as absolute or relative values.

Apart from that, a further segmentation of the surface 102 of the patient can be done in step S4. Particularly, a first surface segment 106 (corresponding to the first portion 106) of the surface of the body part 100 located inside the beam path 110, a second surface segment 108 (corresponding to the second portion 108) of the surface of the body part 100 located outside the beam path 110, and/or a further surface segment 107 of the part 113, which is to be spared in the radiation treatment and which is located inside the beam path 110, can be calculated. Optionally, these surface segments 106, 108, 107 can be displayed and/or color-coded.

Based on the calculations of step S4 and/or the segments 106, 108, 107 determined in step S4, the user or operator may decide when the patient is correctly positioned for the radiation treatment and start the radiation treatment in step S5.

For this purpose, the first portion and/or the first measure can be compared to a threshold, e.g. a clinical threshold, which comparison can indicate when enough amount of surface and/or volume of the body part 100 is located inside the beam path 110. Apart from that, the second portion and/or second measure can be compared to a further threshold. Moreover, a ratio of the first measure and the second measure can be compared to a further threshold value that describes e.g. a ratio of the surface (and/or volume) of the body part 100 located inside the beam path 110 to the surface (and/or volume) of the body part 100 located outside the bam path 110. This comparison or these comparisons can particularly be done automatically, e.g. by the computer 14.

Optionally, at least some, particularly all, of the steps S1 to S4, can be iteratively repeated, and the first portion 106, the second portion 108, the first measure, the second measure and/or the further measure can be computed in real time during movement of the patient, e.g. by means of the patient support unit 26.

Moreover, any of the calculated first segment 106 or first portion 106, the second segment 108 or second portion 108, the first measure, the second measure and/or the further measure can be color-coded and/or visualized e.g. on the graphical user interface 18. By calculating the first portion 106, the second portion, the portion 113, the first measure, the second measure and/or the further measure e.g. in real-time, and by color-coding the patient's surface 102 accordingly, e.g. until the one or more comparisons with one or more threshold values, as described above, signal a valid or correct positioning to the user or operator (e.g. medical staff or a medical technical assistant), the user or operator can be guided to correctly position the patient for the radiation treatment. Therein, the color-coding may comprise displaying the patient surface 102 segmented by the body part 100 and/or the organ to be irradiated, as described with reference to step S1, as well as segmented by the beam path 110, as described with reference to step 3 and/or step S4. For this purpose, different colors and/or different coloring rules may be used.

In the following, certain aspects or details of the exemplary embodiment described with reference to FIG. 4 are summarized. These aspects or details equally apply to any other embodiment. In the embodiment illustrated in FIG. 4, the 3D surface scanner 12 is calibrated to isocenter or isocenter position. Thus, arbitrary entities, such as a part of the patient's surface 102, particularly a surface of the body part 100 can be depicted and/or illustrated relative to the isocenter position. As a consequence, these entities and/or any part of the surface 102 of the patient can be aligned, e.g. rigidly aligned, with the isocenter position and/or with isocenter associated entities. Further, the beam path 110 can be reconstructed based on e.g. isocenter position, collimator, jaws and gantry angle from the planning data or any other parameter as described above. Further, for each point of the surface data it may be checked and/or determined if the point is located inside the beam path 110 or frustum 110 and/or outside the beam path 110 or frustum 110. Each point of the surface data may be labelled accordingly so it can be visualized clearly. Apart from that it can be distinguished between tissue that is in the view of the frustum 110 or inside the beam path 110 and tissue that is not, e.g. by utilizing a segmentation algorithm such as atlas registration or atlas segmentation. This allows to determine or decide if the patient is in a position and posture that is suitable for radiation treatment.

For reconstructing the beam path 110 and intersecting the beam path 110 with the surface as described by the surface data, a relative position between the isocenter position and the surface scanner 12 can be determined and stored e.g. in the storage device 16. For example, a surface scannable phantom can be placed at isocenter position, and the surface image of the phantom can be registered against CAD data of the phantom in order to determine calibration data for the surface scanner 12. Further, the beam path can be reconstructed using at least one of: one or more beam parameters, isocenter information from the planning data (e.g. a beamshape, a relative position of isocenter to a CT image), the isocenter position of the treatment apparatus 22, a gantry angle, and distance of the gantry to the isocenter position, and other parameters as described above.

For the segmentation of the body part 100 or any other desired region of interest, atlas registration or any other segmentation method can be applied. Alternatively or additionally, e.g. surface changes during breathing of the patient derived from a sequence of surface data from the surface scanner 12 can be used for segmentation. Also, segmentation or labelling can be performed manually.

In the following the technical effects associated with at least some of the aforementioned aspects and details are summarized. Having segmented important parts or portions of the surface 102, such as the body part 100, which are to be irradiated in the radiation treatment and which should, therefore, be located inside the beam path 110 (or which are not allowed to be outside the bam path 110 or frustum 110), the amount of surface and/or the amount of volume of the body part 100 located inside the beam path 110 and/or located outside the beam path 110 can be determined, i.e. the first measure, the second measure and/or the further measure can be calculated. Particularly, the amount of surface of the target surface segment 104 located inside the beam path 110 and/or located outside the beam path 110 can be calculated. Apart from that, color-coding can be provided in real-time for instant feedback. This may be as accurate as an isocenter calibration of the 3D surface scanner 12, and therefore more accurate than any CT surface fusion. Moreover, by thresholding the ratio of surface inside the beam path 110 and outside the beam path 110, a beam on signal can be prohibited during monitoring of the patient.

Figure 5:
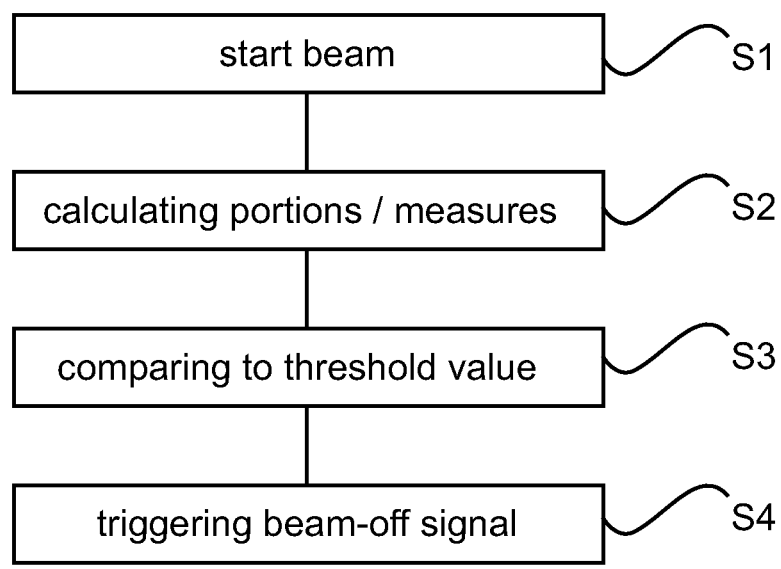
FIG. 5 shows a flowchart illustrating steps of a method of monitoring a position of the patient during the radiation treatment according to an exemplary embodiment of the invention.

FIG. 5 shows a flowchart illustrating steps of a method of monitoring a position of the patient during the radiation treatment according to an exemplary embodiment of the invention. If not stated otherwise, the method described with reference to FIG. 5 comprises the same steps as the methods described with reference to FIGS. 1, 3A, 3B, and 4.

Once the patient is setup and/or positioned, as described with reference to FIG. 4, the beam can be started or switched on in step S1, and the position of the patient can be monitored during the entire radiation treatment. During this monitoring, for each set of surface data acquired with the surface scanner 12, the first portion 106, the second portion 108, the part 113, the first measure, the second measure and/or the further measure can be computed in step S2 based on intersecting the surface 102 and/or surface segments 104, 105, 107 with the beam path 110. The determined first portion 106, the second portion 108, the part 113, the first measure, the second measure and/or the further measure can then be monitored in real-time in step S3. For instance, the amount of surface (and/or volume) of the body part 100 inside the beam path 110, the amount of surface (and/or volume) of the body part 100 outside the beam path 110 and/or the amount of surface (and/or volume) of the part 113 (i.e. healthy tissue) inside the beam path 110 can be monitored and/or compared to one or more threshold values in real-time. Based on this comparison (or these comparisons) a beam-off signal can be triggered in step S5 (or the beam-on signal can be inhibited or suppressed) to switch the radiation beam off, e.g. if one or more of the threshold values are reached or exceeded. Likewise, a beam-on signal can be triggered, e.g. if the one or more of the threshold values are not reached or exceeded, and the beam can be switched on again.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art and practicing the claimed invention, from a study of the drawings, the disclosure, and the appended claims.

In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A computer-implemented method of positioning a patient for a radiation treatment and/or of monitoring a position of the patient during the radiation treatment, the method comprising:
   providing surface data from a 3D surface scanner, wherein the surface data are indicative of a surface of at least a part of a body part of the patient to be irradiated in the radiation treatment, and wherein the surface data are calibrated with respect to a relative position of the 3D surface scanner and an isocenter position of a radiation treatment apparatus;
   reconstructing a beam path of a radiation beam based on planning data for the radiation treatment; and
   calculating, based on intersecting the surface and the reconstructed beam path, at least a first portion of the surface of the body part located inside the beam path and/or at least a second portion of the surface of the body part located outside the beam path.

2. The method according to claim 1, further comprising:
   segmenting the surface data, thereby generating at least one target surface segment of the body part of the patient to be irradiated in the radiation treatment.

3. The method according to claim 2, wherein the calculating at least the first portion of the surface of the body part located inside the beam path and/or at least the second portion of the surface of the body part located outside the beam path comprises:
   calculating a first measure of the at least one target surface segment, wherein the first measure is representative of an amount of surface and/or an amount of volume of the body part located inside the beam path; and/or
   calculating a second measure of the at least one target surface segment, wherein the second measure is representative of an amount of surface and/or an amount of volume of the body part located outside the beam path.

4. The method according to claim 3, further comprising:
   positioning at least the body part of the patient, such that the first measure is maximized and/or the second measure is minimized.

5. The method according to claim 3, further comprising:
   comparing the first measure and/or the second measure to at least one threshold value, wherein the at least one threshold value is indicative of at least one of:
   a minimum amount of surface of the body part located inside the beam path,
   a minimum amount of volume of the body part located inside the beam path,
   a maximum amount of surface of the body part located outside the beam path,
   a maximum amount of volume of the body part located outside the beam path,
   a ratio of an amount of surface of the body part located inside the beam path to an amount of surface of the body part located outside the beam path, and/or
   a ratio of an amount of volume of the body part located inside the beam path to an amount of volume of the body part located outside the beam path.

6. The method according to claim 5, further comprising:
   triggering, based on the comparison of the first measure and/or the second measure with the at least one threshold value, a beam-on signal to switch on the radiation beam or a beam-off signal to switch off the radiation beam.

7. The method according to claim 2, further comprising:
   determining, based on the reconstructed beam path and based on segmenting the surface data, a further measure describing an amount of surface and/or an amount of volume of a further part of the patient, which is to be spared during the radiation treatment and which is located inside the beam path.

8. The method according to claim 1, wherein at least the providing surface data from the 3D surface scanner and the calculating are repeated in an iteration process, and wherein the method further comprises:
   deriving a breathing signal of the patient based on a sequence of calculated first portions of the surface of the body part located inside the beam path and/or based on a sequence of calculated second portions of the surface of the body part located outside the beam path.

9. The method according to claim 1, further comprising: displaying, on a graphical user interface, the reconstructed beam path and the surface of at least the body part of the patient.

10. The method according to claim 9, further comprising: color-coding, on the graphical user interface, the first portion of the surface located inside the beam path and the second portion of the surface located outside the beam path using different colors and/or using at least one coloring rule.

11. The method according to claim 1, wherein the beam path is reconstructed based on one or more of at least one beam parameter describing a direction of the radiation beam, at least one beam parameter describing shape of the radiation beam, the isocenter position, a gantry angle of the radiation treatment apparatus, a distance between a treatment beam source of the radiation treatment apparatus and the isocenter position, an aperture configuration of the treatment beam source, an aperture angle of the treatment beam source, and a collimator configuration of a collimator of the radiation treatment apparatus; and/or
wherein the planning data for the radiation treatment comprise one or more of at least one beam parameter describing the direction of the radiation beam, at least one beam parameter describing t shape of the radiation beam, the isocenter position, the gantry angle of the radiation treatment apparatus, the distance between the treatment beam source of the radiation treatment apparatus and the isocenter position, the aperture configuration of the treatment beam source, the aperture angle of the treatment beam source, and: collimator configuration of the collimator of the radiation treatment apparatus.

12. The method according to claim 1, wherein the body part of the patient to be irradiated in the radiation treatment is at least one of at least a part of a breast of the patient and at least a part of a heel bone of the patient.

13. A computer program product comprising a non-transitory computer readable storage medium storing a computer program containing program instructions, that when executed on at least one processor of the computer or when loaded onto the at least one processor of the computer, causes the computer to perform a method of positioning a patient fro a radiation treatment and/or of monitoring a position of the patient during the radiation treatment, the method comprising:
providing surface data from a 3D surface scanner, wherein the surface data are indicative of a surface of at least a part of a body part of the patient to be irradiated in the radiation treatment, and wherein the surface data are calibrated with respect to a relative position of the 3D surface scanner and an isocenter position of a radiation treatment apparatus:
reconstructing a beam path of a radiation beam based on planning data for the radiation treatment; and
calculating, based on intersecting the surface and the reconstructed beam path, at least a first portion of the surface of the body part located inside the beam path and/or at least a second portion of the surface of the body part located outside the beam path.

14. A medical system, comprising:
at least one computer comprising a processor device;
at least one electronic data storage device storage surface data and/or planning data; and
a medical device for carrying out a medical procedure on a patient,
wherein the at least one computer is configured to perform a method of positioning the patient for a radiation treatment and/or of monitoring a position of the patient during the radiation treatment, including:
providing surface data from a 3D surface scanner, wherein the surface data are indicative of a surface of at least a part of a body part of the patient to be irradiated in the radiation treatment, and wherein the surface data are calibrated with respect to a relative position of the 3D surface scanner and an isocenter position of a radiation treatment apparatus:
reconstructing a beam path of a radiation beam based on planning data for the radiation treatment; and
calculating, based on intersecting the surface and the reconstructed beam path, at least a first portion of the surface of the body part located inside the beam path and/or at least a second portion of the surface of the body part located outside the beam path,
wherein the at least one computer is operably coupled with:
the at least one electronic data storage device for acquiring, from the at least one electronic data storage device, at least the surface data and/or the planning data, and
the medical device for issuing a control signal to the medical device for controlling operation of the medical device based on the calculated first portion of the surface of the body part located inside the beam path and/or the calculated second portion of the surface of the body part location outside the beam path.

15. The system according to claim 14, wherein the system further comprises the 3D surface scanner for acquiring surface data of at least a part of the patient, and/or wherein the medical device comprises:
a radiation treatment apparatus comprising a treatment beam source and a patient support unit,
wherein the at least one computer is operably coupled with the radiation treatment apparatus for issuing a control signal to the radiation treatment apparatus for controlling, based on the calculated first portion and/or based on the calculated second portion, at least one or more of:
an operation of the treatment beam source, and/or
a position of the patient support unit.

* * * * *